United States Patent [19]
Reddington et al.

[11] Patent Number: 5,877,310
[45] Date of Patent: Mar. 2, 1999

[54] GLYCOCONJUGATED FLUORESCENT LABELING REAGENTS

[75] Inventors: Mark V. Reddington; Alan S. Waggoner, both of Pittsburgh, Pa.

[73] Assignee: Carnegie Mellon University, Pittsburgh, Pa.

[21] Appl. No.: 847,482

[22] Filed: Apr. 25, 1997

[51] Int. Cl.$^6$ .......................... C07H 21/02; C07H 17/08; O07H 21/04; G01N 33/53
[52] U.S. Cl. ...................... 536/25.32; 530/802; 536/6.5; 435/7.8; 548/455
[58] Field of Search ................................ 536/6.5, 25.32; 530/802; 435/7.8; 548/455

[56] References Cited

U.S. PATENT DOCUMENTS

| | | | |
|---|---|---|---|
| 4,259,233 | 3/1981 | Carrico et al. | 260/112 B |
| 4,621,911 | 11/1986 | Lanni et al. | 350/524 |
| 4,933,948 | 6/1990 | Herkstroeter | 372/53 |
| 4,966,607 | 10/1990 | Shinoki et al. | 8/549 |
| 4,981,977 | 1/1991 | Southwick et al. | 548/455 |
| 5,268,486 | 12/1993 | Waggoner et al. | 548/427 |
| 5,316,906 | 5/1994 | Haugland et al. | 435/4 |
| 5,486,616 | 1/1996 | Waggoner et al. | 548/217 |

FOREIGN PATENT DOCUMENTS

| | | |
|---|---|---|
| 0 047 459 | 8/1981 | European Pat. Off. . |
| 2 302 094 | 1/1997 | United Kingdom . |
| WO95/02700 | 1/1995 | WIPO . |

OTHER PUBLICATIONS

Bannwarth et al, "Formation of Carboxamides with N,N,N',N'–Tetramethyl *Succinimido) Uromium Tetrafluoroborate in Aqueous / Organic Solvent Systems", *Tetrahedron Letters*, vol. 32, No. 9, pp.1157–1160 (1991).

Singh et al, "Controlled Coupling of Aminoglycoside Antibiotics to Prietins for use in Homogeneous Enzyme Innumoassays",*Can. J. Chem.*, vol.62 (1984),pp. 2471–2477.

Whitaker et al, "Cascade Blue Derivatives: Water Soluble, Reactive, Blue Emisison Dyes Evaluated as Fluorescent Labels and Tracers",*Analytical Biochemistry*198, 119–130 (1991).

Derwent Publication, XP002077545, 30 Oct. 1992, "Water Soluble Derivative Preparation React Derivative Beta Cyclodextrin Carbozymethyl Beta Cyclodextrin Dissolve Product Water Boiling Filter"(1 page).

Reddington, "New Glycoconjugated Cyanine Dyes as Fluorescent Labeling Reagents", *J. Chem. Soc. Perkin Trans. 1*.No. 1. 1998, pp. 143–147.

Guether et al, "Photostable Cyanine Dye β–Cyclodextrin Conjugates",*Tetrahedon Letters*, vol. 38, No. 35, pp.6167–6170 (1997).

J. Chem. Soc. Faraday Trans 1994, 90(23) 3517–3520 Matsuzawa et al Light Stability of a β–cyclodextrin†Inclusion Complex of a Cyanine Dye.

Research News Adv Mater 1993, 5, No. 2 Akihiko Ueno Fluorescent Sensors and Color–Change Indicators for Molecules.

*Primary Examiner*—Floyd D. Higel
*Attorney, Agent, or Firm*—Nixon & Vanderhye

[57] ABSTRACT

Water soluble glycoconjugated fluorescent labeling reagents comprised of a fluorescent dye, one or more sugar or carbohydrate residues that impart water solubility, and a reactive group that allows covalent attachment of the reagent to a substrate are disclosed. Glycoconjugated fluorescent labeling reagents are depicted as follows:

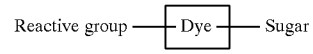

These glycoconjugates are highly water soluble because of the sugar residues. This property is expected to lower nonspecific binding to cellular matter, reduce precipitation of labeled substrates, inhibit quenching of fluorescence, and unlike many prior fluorescent labeling reagents, that are soluble only in organic solvents, render the glycoconjugates usable in wholly aqueous solution.

1 Claim, 5 Drawing Sheets

GLYCOCONJUGATED FLUORESCENT LABELING REAGENTS

This invention was made under grant MCB-890118 of The National Science Foundation

BACKGROUND OF THE INVENTION

This invention relates to water-soluble fluorescent labeling reagents for biological investigations. Fluorescence detection techniques are dependent on the physical characteristics of the dyes that they employ. Many dyes that have excellent photophysical properties (high extinction coefficients and high quantum yields) have limited utility because other properties such as water solubility and photostability are poor. In particular, for most biological applications good aqueous solubility for the fluorophore is crucial.

A common problem with many commercially available fluorescent labeling reagents is that they are not made water soluble thus they must be dissolved in organic solvents, such as DMF, prior to substrate labeling in aqueous media. Such organic solvents can have a deleterious effect upon sensitive substrates. The solubility of organic dyes affects the degree to which they interact with themselves in solution and when conjugated to substrates and therefore directly influences their light absorption and emission properties. The problem of non specific staining of cellular matter by the dye, which reduces signal to noise during observation, is also a function of the dye's hydrophobicity and of the polarity of its appended functional groups. In addition, the dye should not cause precipitation of the substrate once labeling has occurred. There is a need for fluorescent reagents that are bright, that have good aqueous solubility, and that give low non specific staining.

In recent years, a series of reagents based sulphocyanine dyes has become commercially available; see U.S. Pat. Nos. 5,268,486 and 5,486,616 the disclosures of which are hereby incorporated by reference. These dyes, which are highly polar due to the presence of two sulphonic acid residues, have excellent photophysical properties combined with good aqueous solubility. To determine if further improvements could be achieved for the properties of cyanine dye based fluorescent reagents, the sulphonic acid groups were replaced with carbohydrate residues to create water soluble cyanine dyes with reduced polarity and labeling capabilities for biological and non-biological substrates.

DETAILED DESCRIPTION OF THE INVENTION

Figure 1:
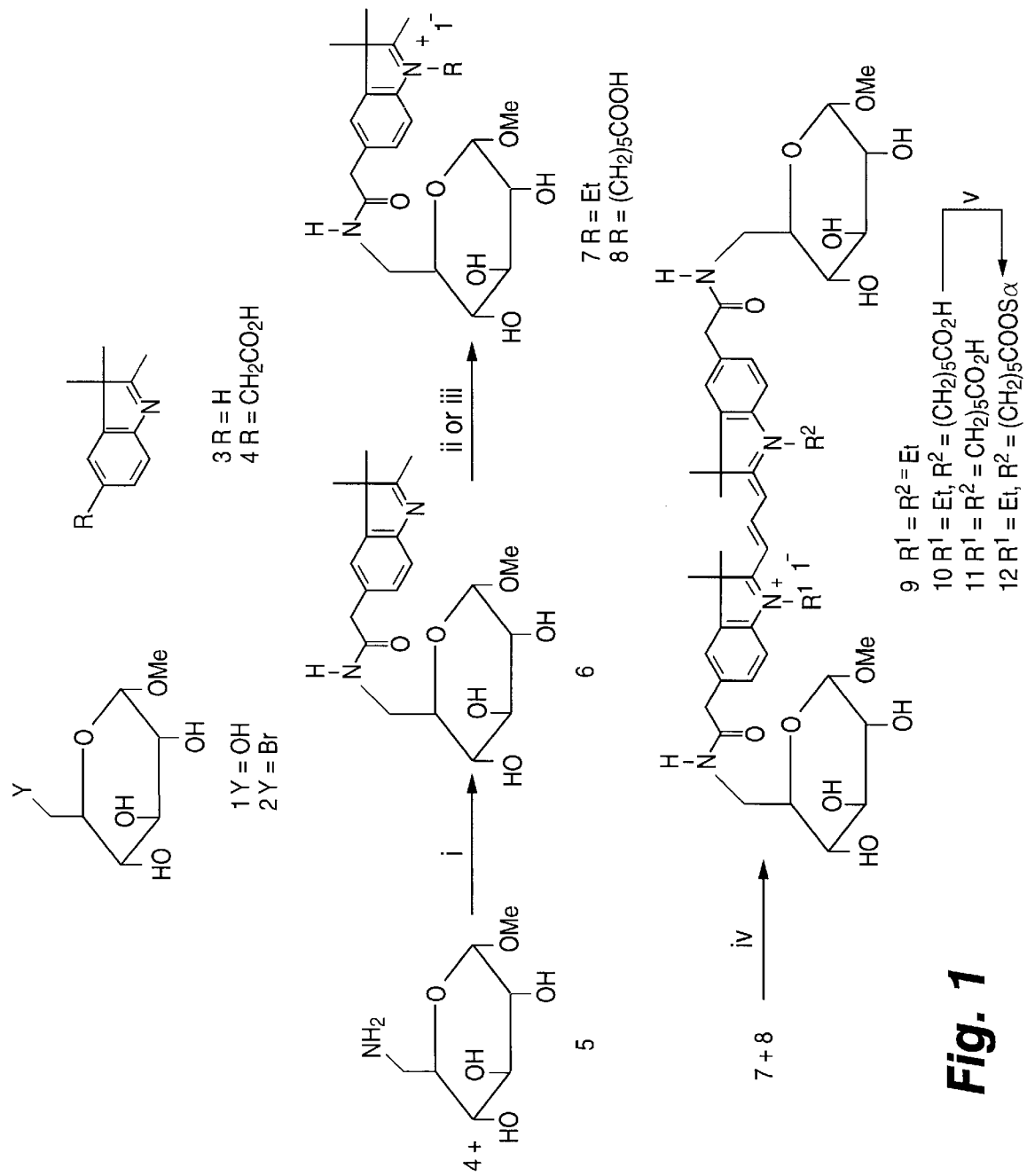
FIG. 1 is a flow chart illustrating the preparation of some water soluble fluorescent labeling reagents of the present invention.
Figure 2:
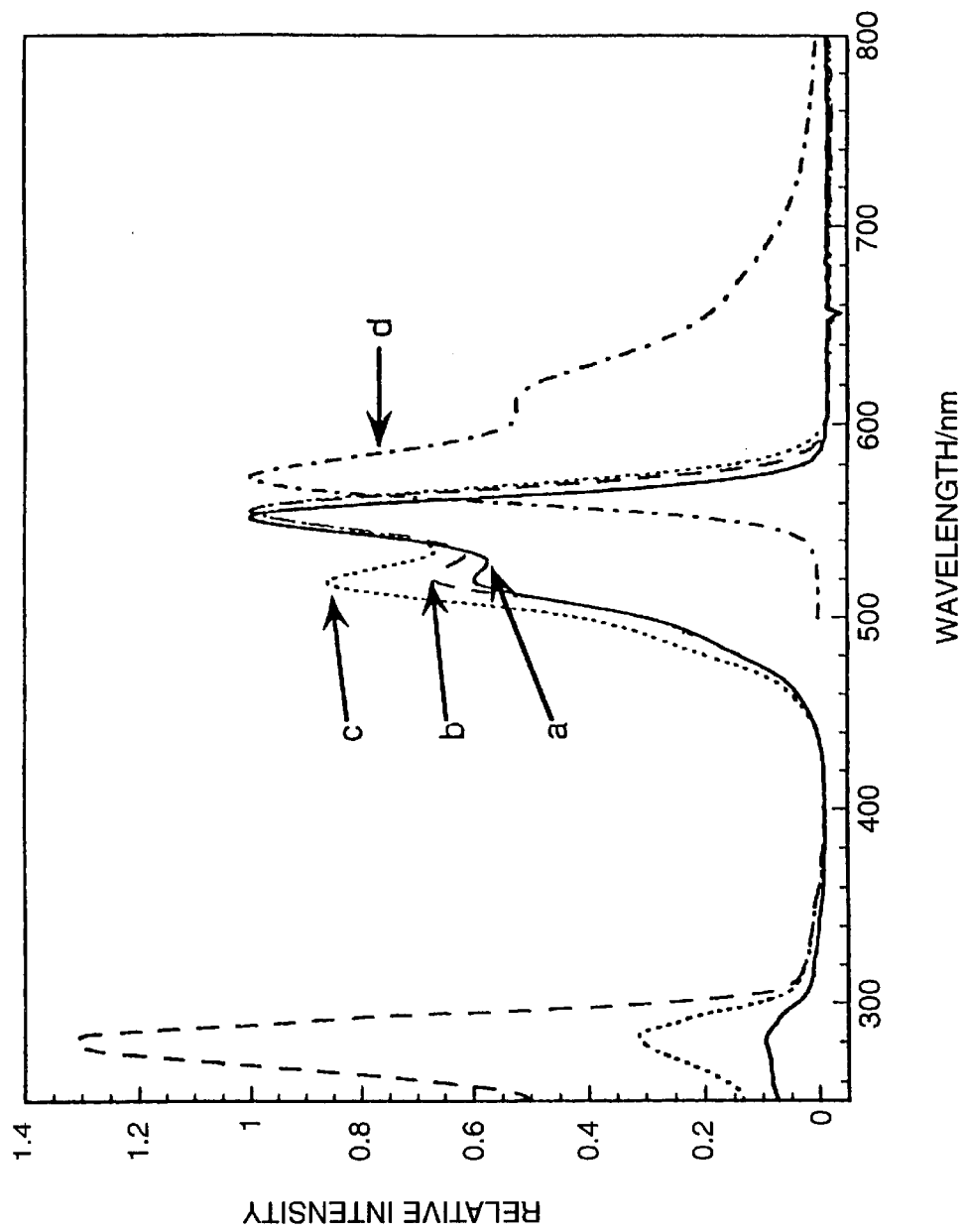
FIG. 2 is a graph displaying absorption and emission spectra of protein labeled with a glycoconjugated cyanine dye reagent of the first preferred embodiment.

This invention relates to water soluble fluorescent labeling reagents that are comprised of a fluorescent dye, one or more sugar or carbohydrate residues that impart water solubility, and a reactive group that allows covalent attachment of the reagent to a substrate. For the purposes of this patent, such a reagent is termed a glycoconjugated fluorescent labeling reagent and is depicted as follows:

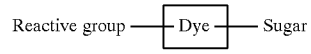

These glycoconjugates are highly water soluble because of the sugar residues. This property is expected to lower non specific binding to cellular matter, reduce precipitation of labeled substrates, inhibit quenching of fluorescence, and unlike many prior fluorescent labeling reagents, that are soluble only in organic solvents, render the glycoconjugates usable in wholly aqueous solution.

The sugar or carbohydrate moiety of the glycoconjugate may be a monosaccharide, disaccharide, trisaccharide, an oligosaccharide such as cyclodextrins, or a polysaccharide, such as a dextran or a ficol. The monosaccharide units of the larger sugars may be arranged in a linear or branched manner. The sugar may be charged or non charged. Of particular interest are the cyclodextrins, a series of cyclic oligosaccharides composed of 6 or more α-(1,4) linked D(+)-glucopyranose units, since in addition to providing aqueous solubility, they may increase the photostability of the fluorescent dye. Reagents utilizing lower molecular weight sugars will have greater membrane permeability, tissue penetration and will perturb the properties of the labeled substrate to a lesser degree than those which utilize large sugars.

Fluorescent dyes are generally known and used for detection and imaging of biological and non biological substrates. The dye or fluorophore of the glycoconjugate may be any of the fluorescent dyes commonly used for labeling purposes. The absorption and emission wavelengths of the dye are not restricted to a particular region of the spectrum but may be anywhere from the near UV through the near IR region or beyond these extremes. The absorption and emission properties may be or may not be sensitive to environmental factors such as polarity, pH, and ionic strength. The basic dye structure must contain sufficient functionality to allow for the incorporation of the sugar residue(s) either during or after dye synthesis, and for incorporation of the reactive group. Examples of such dyes include but are not limited to polycyclic dyes such as pyrene, polyheterocyclic dyes, coumarin dyes, xanthene dyes such as fluorescein and rhodamine, polyene dyes, styryl dyes, polymethine dyes, merocyanine dyes and ketocyanine dyes. Other suitable fluorophores are disclosed in U.S. Pat. Nos. 4,621,911; 4,933,948; 4,981,977; 5,268,486 and 5,486,616 (the disclosures of which are hereby incorporated by reference) among others. Of particular interest are the cyanine dyes because this class of dyes is increasingly being used for fluorescent labeling and because a method for incorporation of the sugar and reactive group into one of these dyes is applicable to many others dyes of this class. Such dyes described above are compatible with existing detection and imaging technologies.

A typical method for labeling of substrates with fluorescent dyes is to form a covalent bond between suitable groups on the dye and compatible groups on the substrate. The present invention also relates to labeling methods wherein the glycoconjugates of the present invention covalently react with a substrate possessing one or more functional groups. The substrate may be incubated with an amount of a glycoconjugate under conditions and for a period of time sufficient to permit covalent bond formation between them. Thus the labeled substrate is rendered detectable by fluorescence detection methods.

The glycoconjugate may include or be modified to include a reactive group that can be used in labeling reactions with complimentary functional groups in the substrate. The reactive group should not react with any portion of the glycoconjugate or, if it does then, it should do so at a rate that is significantly slower than the rate of labeling of the intended complimentary functionality on the substrate.

There are three possible modes of forming the covalent bond between reagent and substrate. They are:

Dye - R+G - substrate→Dye - substrate

Dye - G+R - substrate→Dye - substrate

Dye - G+F - substrate+X→Dye - substrate where R is the "reactive" group, G and F are complimentary groups and X is some coupling reagent. Examples of reactive groups (R) include but are not limited to succinimidyl ester, carboxylic acid, isothiocyanate, haloacetamide, maleimide, alkyl halide, azido, hydrazido, aldehyde, ketone, amino, or sulphydryl. Complimentary functional groups (G or F) include but are not limited to carboxylic acid, aldehyde, ketone, amino, or sulphydryl. X May be any commonly used coupling reagent, e.g. a carbodiimide.

The glycoconjugate may also contain other chemical or structural groups that influence dye aggregation, light absorption and emission properties and/or photostability, but these groups should not adversely influence the labeling reaction described herein. Such groups include but are not limited to alkyl, aryl, amino, hydroxyl, halo, nitro, cyano, quaternary ammonium, guanidinium, or phosphate.

The glycoconjugates of this invention have a wide variety of applications including as labels, probes for materials of interest, ion tracers, pH indicators and tracers for cell labeling. Biological substrates that may be labeled include proteins, peptides, antibodies, nucleic acids (DNA, RNA), drugs, carbohydrates, lipids, hormones, toxins, cells, microbial materials, and tissues. Applications involving non biological substrates include targeting of cellulose based materials (including for example papers), textiles, petroleum based products, polymers, particles and gel filtration and chromatographic media.

Reaction of the glycoconjugate with a substrate renders the substrate detectable by fluorescence microscopy, fluorescence immunoassay, fluorescence spectrophotometry, flow cytometry, DNA sequencers, capillary electrophoresis instruments, fluorescent gel readers or other fluorescence based detection systems. The labeled material may also be detected by light absorption techniques such as absorption spectrophotometry.

In addition to the foregoing one-step labeling process, the present invention also relates to two-step labeling processes in which, in a first step, a compound of the present invention covalently reacts with and thereby labels a primary component, such as an antibody. In a second or staining step of the two-step procedure, the fluorescently labeled primary component is then used as a probe for a secondary component, such as an antigen for which the antibody is specific. When the target of the so-labeled antibodies is a cell, the second step of the procedure may be used to determine the amount of labeled antibodies which are attached to that type of cell by determining the intensity of the fluorescence of the cells. By this two-step procedure, monoclonal antibodies and other components covalently labeled in the first step with the fluorescent compounds of the present invention could be used as antigen probes.

The compounds of the present invention can also be used to determine the concentration of a particular protein or other component in a system. If the number of reactive groups on a protein which can react with a probe is known, the fluorescence per molecule can be known and the concentration of these molecules in the system can be determined by the total fluorescence intensity of the system. This particular method can be used to measure the concentration of various labeled analytes using microtitre plate readers or other known immunofluorescence detection systems. The concentration of fluorescently labeled material can also be determined using, for example, fluorescence polarization detection instruments.

The glycoconjugates of the present invention can also be used in a detection method wherein a plurality of the glycoconjugates are covalently attached to a plurality of different primary components, such as antibodies, each primary component being specific for a different secondary component, such as an antigen, in order to identify each of a plurality of secondary components in a mixture of secondary components. According to this method of use, each of the primary components is separately labeled with a fluorescent compound having a different light absorption and emission wavelength characteristic compared with the dye molecules used for labeling the other primary components. The so-called primary components are then added to the preparation containing secondary components, such as antigens, and the primary components are allowed to attach to the respective secondary components for which they are selective. Any unreacted probe materials may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochrometers to select the rays of the excitation wavelength and to select the wavelengths of fluorescence is next employed to determined the intensity of the emission wavelengths corresponding to the fluorescent compounds utilized, the intensity of fluorescence indicating the quantity of the secondary component which has been bound with a particular labeled primary component. Known techniques for conducting multi-parameter fluorescence studies include, for example, multi-parameter flow cytometry.

In certain cases a single wavelength of excitation can be used to excite fluorescence from two or more materials in a mixture where each fluoresces at a different wavelength and the quantity of each labeled species can be measured by detecting its individual fluorescence intensity at its respective emission wavelength. If desired, a light absorption method can also be employed.

The detection method of the present invention can be applied to any system in which the creation of a fluorescent primary component is possible. For example, an appropriately reactive fluorescent compound can be conjugated to a DNA or RNA fragment and the resultant conjugate then caused to bind to a complementary target strand of DNA or RNA. Appropriate fluorescence detection equipment can then be employed to detect the presence of bound fluorescent conjugates.

The present invention also relates to the covalent reaction between compounds of the present invention, and amine, aldehyde, sulphydryl, phosphoryl or other known functional groups on materials such as, for example, proteins, peptides, carbohydrates, nucleic acids, derivatized nucleic acids, lipids, certain other biological molecules, biological cells, soluble polymers, polymeric particles, polymer surfaces, polymer membranes, glass surfaces and other particles and surfaces. Because detecting fluorescence involves highly sensitive optical techniques, the presence of these dye "labels" can be detected and quantitated even when the label is present in very low amounts. Thus, the dye labeling reagents can be used to measure the quantity of a material that has been labeled.

DESCRIPTION OF THE PREFERRED EMBODIMENTS

Figure 3:
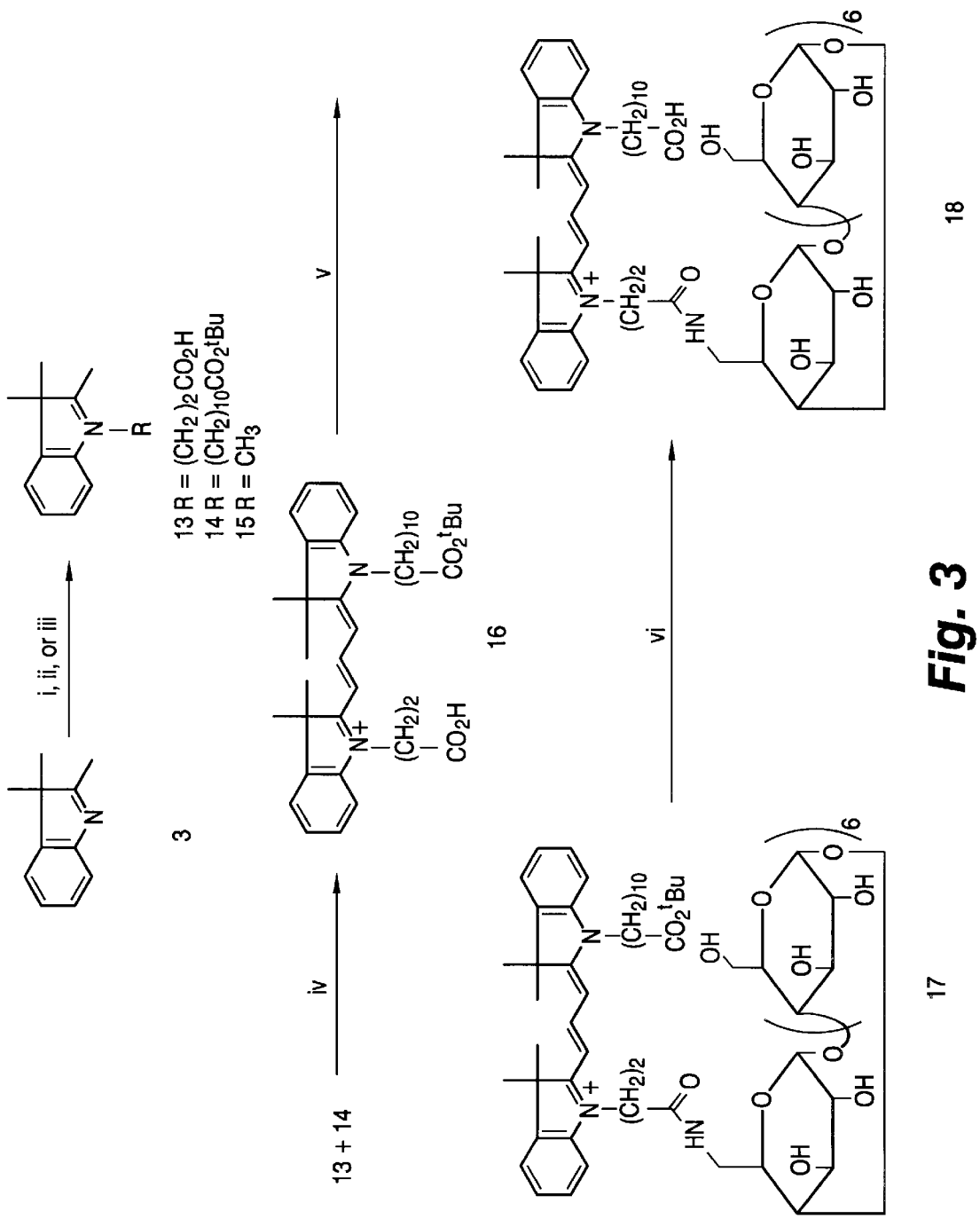
FIG. 3 is a flow chart illustrating the preparation of a glycoconjugated reagent in which the sugar residue is β-cyclodextrin, the fluorophore is a cyanine dye and which contains a carboxylic acid group.
Figure 4:
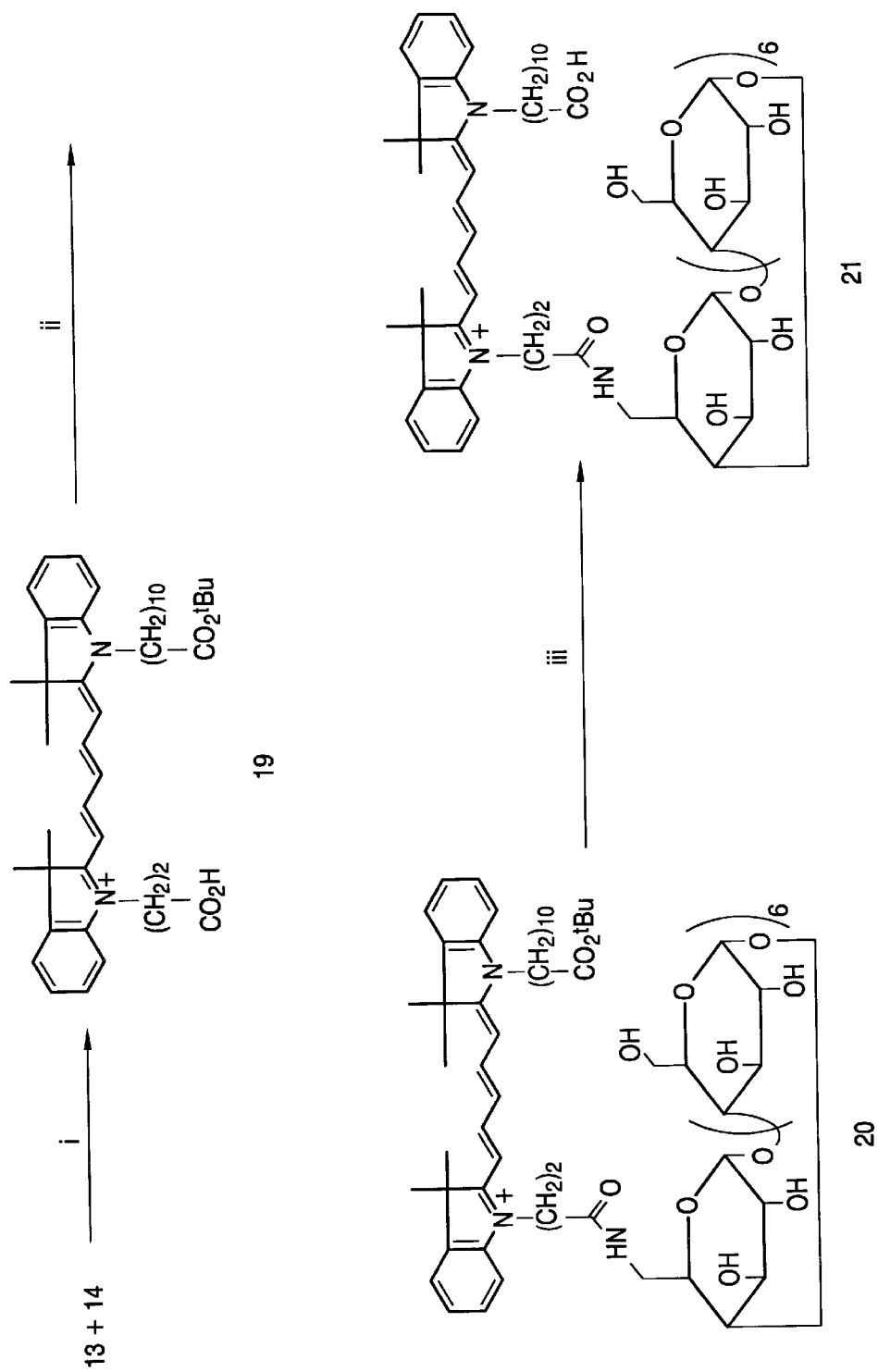
FIG. 4 is a flow chart illustrating the preparation of a glycoconjugated reagent in which the sugar residue is β-cyclodextrin, the fluorophore is a cyanine dye and which contains a carboxylic acid group.
Figure 5:
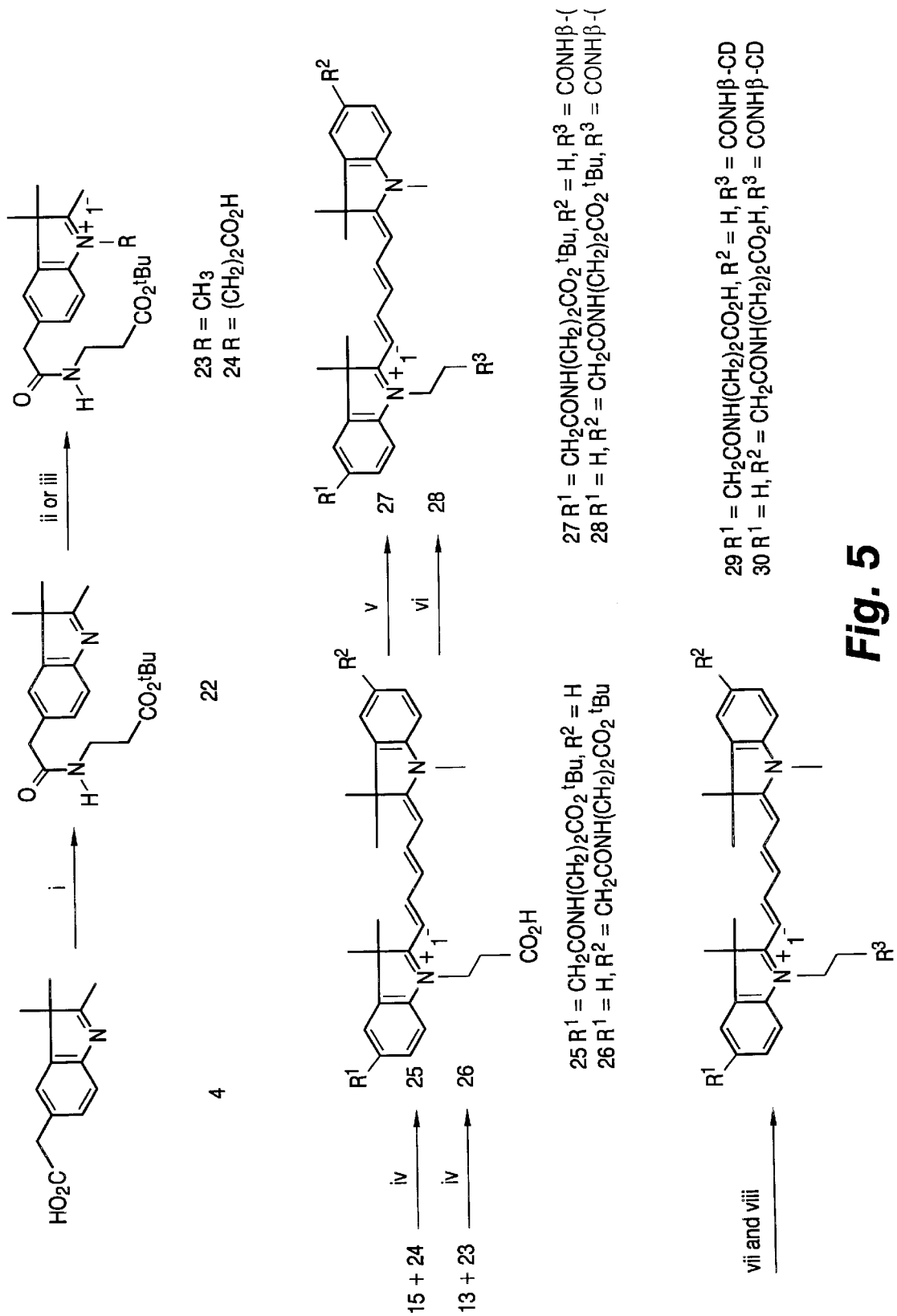
FIG. 5 is a flow chart illustrating the preparation of two glycoconjugated reagents in which the sugar residue is β-cyclodextrin, the fluorophore is a cyanine dye and which contain a carboxylic acid group.

The invention is further described with reference to the attached drawings and flowcharts. Examples of water-soluble fluorescent labeling reagents of this invention are prepared as depicted in FIGS. 1, 3, 4, and 5.

In the first preferred embodiment methylglucopyranoside 1 was chosen to be the water solubilizing residue, for a cyanine dye fluorophore, because its glycosidic linkage is fixed and because of its ease of derivatization without recourse to any protecting group chemistry. Alkylation of the heterocyclic precursors to cyanine dyes using a halogenated or a sulphonate ester derivative of 1 offers the simplest method for introduction of the sugar and creates a link that will not be cleaved readily by enzymes in biological environments, thus ensuring a stable labeling reagent. 6-Bromo-6-deoxymethyl-α-glucopyranoside 2 was prepared using NBS and $PPh_3$, but treatment of trimethylindolenine 3 or carboxymethyltrimethylindolenine 4 with 2 proved unsatisfactory as a method to introduce the carbohydrate residue, due to low yields. Consequently, an alternative route involving the formation of an amide link was used. 6-Azido-6-deoxymethyl-α-glucopyranoside was prepared from 1 in a two step one pot process using $NBS/PPh_3$ followed by treatment with sodium azide, and the azide was then reduced to 6-amino-6-deoxymethyl-α-glucopyranoside 5 using $PPh_3$ and concentrated aqueous ammonia. Slight modifications to the literature procedures were made to allow more rapid attainment of the amine 5 and are described below. Coupling of carboxymethylindolenine 4 with amine 5 gave the key indoleninemethylglycoside intermediate 6 in 92% yield. Alkylation of 6 allows for the introduction of a variety of functional groups (e.g. $CO_2H$, OH, SH, $NH_2$) prior to dye formation. Treatment of 6 with iodoethane in acetonitrile or with iodohexanoic acid in nitromethane afforded the hygroscopic quaternary indolenium dye precursors 7 and 8 in 86% and 80% yields, respectively. Purification of precursor 8 by either silica gel or C18 reversed phase silica gel chromatography is made difficult by the compound's poor stability. Collected fractions of 8 turned pink/red after only a few minutes standing open to the atmosphere. Once the solvents were removed from these fractions the solid residues continued to darken. Dye precursor 7 showed similar instability. Consequently, the crude compounds were used in the following reactions. Condensation of equimolar portions of 7 and 8 with triethylorthoformate in pyridine afforded a mixture of three indocyanine dyes 9, 10, and 11. The unsymmetrical dye 10 was isolated by reversed phase chromatography, in 24% yield. The symmetrical dyes 9 and 11 are more easily obtained by self condensation of 7 and 8, respectively. Reaction of dye 10 with tetramethyl(succinimido)uronium tetrafluoroborate (TSTU) in DMF afforded the succinimidyl active ester 12, which can be used to label amine containing substrates.

The active ester 12 was readily soluble in water and did not show appreciable hydrolysis at neutral pH, or self condensation, over a period of 16 hours. Thus, no organic solvents are required for labeling of biological substrates with 12, in aqueous media. Active ester 12 was conjugated to aminodextrans and to sheep immuno-γ-globulin (IgG) to provide a range of labeling densities on the antibody. A labeling efficiency of greater than 40% was observed in phosphate buffered saline (PBS) at pH 9.5. Precipitation of the protein was observed only when greater than 6–7 dyes were attached to it.

The absorption and fluorescent properties of dyes 9, 10, and 11 and the labeled dextran are shown in Table 1.

TABLE 1

Absorption and fluorescence data of dyes 9, 10, 11 and Cy3.29 and labeled substrates.

| Dye | Solvent | Absorption Max/nm | Emission Max/nm | $\phi_f$ |
|---|---|---|---|---|
| 9 | water | 550 | 564 | 0.04 |
|  | ethanol | 560 | 576 | 0.10 |
|  | DMSO | 564 | 581 | 0.20 |
| 10 | water | 552 | 576 | 0.06 |
|  | PBS | 552 | — | 0.06 |
|  | ethanol | 560 | 577 | 0.12 |
|  | DMSO | 566 | 582 | 0.23 |
| 11 | water | 552 | 569 | 0.08 |
|  | ethanol | 562 | 577 | 0.16 |
|  | DMSO | 566 | 583 | 0.28 |
| 10-Dextran | water | 554 | 571 | 0.10 |
| Cy3.29 | PBS | 550 | 565 | 0.05 |
| Cy3.29-IgG | PBS |  |  | 0.10 |

PBS: Phosphate Buffered Saline

Attachment of the carbohydrate residues does not appreciably change the basic indocyanine absorption and fluorescence properties compared to the commercial dye Cy3.29. The wavelengths of the absorption and fluorescence bands are relatively solvent insensitive. Increasing solvent viscosity reduces conformational mobility of the excited dye and lowers non radiative energy loss. Thus there is an increase in quantum yields of fluorescence ($\phi_f$) along the series water<ethanol<DMSO. Reduced conformational mobility with increasing size of the side chains on the chromophore is responsible for the increase in $\phi_f$ along the series 9<10<11<labeled dextran. The absorption spectra of the dyes are nearly identical to their fluorescence excitation spectra indicating that ground state dye-dye interactions are insignificant. The carbohydrate residues provide sufficient aqueous solubility to prevent aggregation of the organic fluorophores in aqueous solution. The labeled dextran showed similar properties to dye 10, however, the ratio of the absorption maximum at 552 nm to the shoulder at 522 nm is decreased slightly compared to that of dye 10.

When conjugated to antibody the photophysical properties of the dye are dependent on its labeling density as shown in Table 2.

TABLE 2

Absorption and fluorescence data for 10-IgG conjugates in PBS.

| Dye/Protein | $A_{552}/A_{522}$ | $\emptyset_f$ | AB/1000 |
|---|---|---|---|
| 0.64 | 1.55 | 0.19 | 15 |
| 1.0 | 1.50 | 0.18 | 24 |
| 2.1 | 1.40 | 0.15 | 40 |
| 2.9 | 1.33 | 0.12 | 45 |
| 3.8 | 1.27 | 0.09 | 45 |
| 4.7 | 1.25 | 0.09 | 52 |
| 5.2 | 1.20 | 0.08 | 52 |
| 5.7 | 1.18 | 0.06 | 47 |
| 6.1 | 1.17 | 0.06 | 50 |

AB: Antibody Brightness

At low dye to protein ratios the absorption properties resemble those of dye 10 and of the labeled dextran, but the quantum yields are higher than that of 10 because of reduced conformational mobility when the dye is attached to the surface of the protein. As the labeling density increases the ratio of the absorbance maximum at 552 nm to that at 522 decreases in accord with increasing formation of intramolecular dye dimers and aggregates on the protein surface. These aggregates have greatly reduced quantum yields compared to the monomeric dye. Thus, the quantum yield of the labeled protein decreases as the labeling density increases. A maximum antibody brightness (AB=no. of dyes.$\phi$f.$\epsilon$) is achieved with a labeling density of 4–5 dyes per antibody. At low labeling densities antibody labeled with dye 10 has a higher quantum yield and is brighter than antibody labeled with Cy3.29.

The long term stability of these active ester reagents is of concern due to the possibility of ester formation between the active ester functionality and the hydroxyl groups of the sugar. No noticeable deterioration was observed to the reagent when it was stored at room temperature under anhydrous conditions for a period of 5 months.

In summary, the new cyanine dye labeling reagents of the first preferred embodiment are highly water soluble, easily synthesized, and have spectral properties similar to their non glycoconjugated analogs. They can be conjugated to amine containing substrates such as antibodies and dextrans with relatively high efficiencies to give brightly labeled substrates.

In the second preferred embodiment (compound 18 in FIG. 3), β-cyclodextrin was chosen as the water solubilizing sugar residue. The fluorophore is a cyanine dye, and the reactive group can be generated from the carboxylic acid group either by a preactivation step or in situ with the substrate as described in the general procedures.

In the third preferred embodiment (compound 21 in FIG. 4), β-cyclodextrin was chosen as the water solubilizing sugar residue. The fluorophore is a cyanine dye that has absorption and emission wavelengths longer than those of the dyes of the first two preferred embodiments. The reactive group can be generated from the carboxylic acid group either by a preactivation step or in situ with the substrate as described in the general procedures.

In the fourth preferred embodiment (compounds 29 and 30 in FIG. 5), β-cyclodextrin was chosen as the water solubilising sugar residue. The fluorophore is the same cyanine dye of the third preferred embodiment. The two reagents described differ from each other and from that of the third preferred embodiment by the site of attachment of the carboxylic acid group that is used to generate the reactive group.

The compounds identified by number above and depicted in the attached flow diagrams were prepared as follows:

Experimental

General

All reagents and solvents were obtained from either Aldrich, Sigma, Kodak, or Fisher, and were used as received unless otherwise stated. Amino dextran refers to that of m.w. 40,000 with 7.2 amino groups per dextran, and was obtained from Molecular Probes. Solvents were dried according to standard literature procedures. NMR spectra were recorded on an IBM 300 MHz spectrometer and were referenced using the residual solvent signal ($CD_3CN$:1.93, $(CD_3)_2CO$: 2.03, $CDCl_3$: 7.26, $D_2O$: 4.65, and mixtures of $D_2O$ with either $CD_3CN$ or $(CD_3)_2CO$: 1.93 and 2.03 for the organic solvent respectively). Absorption spectra were recorded on a Hewlett-Packard HP8452 diode array spectrophotometer and fluorescence spectra were recorded on a SPEX Fluorolog 2 spectrometer. Quantum yields were determined using rhodamine 6G ($\phi_f$=0.95 in ethanol) as a standard. Melting points were recorded on an Electrothermal apparatus and are uncorrected. Flash chromatography refers to the procedure of Still et al [J. Org. Chem., 1978, 43, 2923] and was performed on either silica gel 60 (Baker) or C18 bonded silica gel (Analtech). TLC was performed on either silica gel 60 (Merck) or C18 impregnated silica gel (Analtech) glass plates.

6-Deoxy-6-amino-methyl-α-glucopyranoside 5

To a dry 500 ml flask, under argon, was added an efficient stirring bar, 1 (10.2 g, 52.6 mmol), PPh$_3$ (27.6 g, 105 mmol), and dry DMF (250 ml). The mixture was cooled in an ice bath. NBS (18.9 g, 106 mmol) was added and the mixture was stirred at 0° C. for 20 minutes. The ice bath was replaced with an oil bath and the mixture was heated at 55° C. for 3 hours. Methanol (10 ml) was added and the mixture was stirred for a further 10 minutes. Sodium azide (20.4 g, 314 mmol) was added and the mixture was heated at 85° C. for 4 hours. The solvent was removed under high vacuum and the residue was partitioned between water (250 ml) and methylene chloride (200 ml). The aqueous phase was washed twice more with methylene chloride (2×200 ml) and was filtered. The aqueous solution was passed through a column of AG 501 mixed bed ion exchange resin (350 g). The resin was washed with water (400 ml). The combined aqueous solutions were evaporated in vacuo and the residue was dried under high vacuum over $P_2O_5$ overnight, in a 500 ml flask. PPh$_3$ (39.0 g, 148 mmol) and dry DMF (200 ml) were added to the flask and the mixture was stirred at room temperature, under argon, for 2 hours. Concentrated aqueous ammonia (40 ml) was added to the reaction mixture and stirring was continued for 20 hours. The volatile components were removed under high vacuum and the residue was partitioned between water (300 ml) and methylene chloride (300 ml). The aqueous phase was washed twice more with methylene chloride (2×200 ml) and was filtered. The aqueous solution was passed through a column of Dowex 50 (8X) strongly acidic cation exchange resin (H-form) (4×12 cm). The resin was washed with water (400 ml), methanol (1 L), water (400 ml), and 2M aqueous ammonia (500 ml). The ammonia containing eluant was collected and evaporated in vacuo to afford amine 5 as an off white hygroscopic solid (6.23 g, 62%); $\delta_H$ ($D_2O$) 2.60 (1H, dd, J 6.7 and 13.7, H-6), 2.85 (1H, dd, J 2.6 and 13.7, H-6), 3.14 (1H, dd, J 9.8 and 8.8, H-3), 3.27 (3H, s, OCH$_3$), 3.38–3.53 (3H, m, H-2 ,H-3, and H-4); m/z (FAB) 216.0 (M+H), 238.0 (M+Na), 198.9, 172.8.

N-(3,4,5-Trihydroxy-6-methoxy-tetrahydropyan-2-ylmethyl)-2-(2,3,3-trimethyl-3H-indol-5-yl) acetamide 6

To a dry 25 ml flask, under argon, was added a stirring bar, 4 (111 mg, 0.51 mmol), dicyclohexylcarbodiimide (159 mg, 0.77 mmol), and N-hydroxy-succinimide (118 mg, 1.0 mmol). The flask was cooled in an ice bath for 5 minutes and then dry DMF (2 ml) was added. The mixture was stirred at 0° C. for 8 hours, and then at 4° C. (in refrigerator) for 72 hours. The solid was filtered off and was washed with DMF (1 ml). The combined DMF solutions were evaporated under high vacuum. The residue was taken up in acetonitrile (1.5 ml) and was filtered. The acetonitrile was removed in vacuo to afford the succinimidyl ester of 4, which was used without further purification. The active ester was dissolved in dry DMF (0.5 ml) and was added to a mixture of amine 5 (150 mg, 0.75 mmol) and triethylamine (0.10 ml) in dry DMF (1.0 ml). The mixture was stirred at 40° C. overnight. The volatile components were removed under high vacuum to afford a pale orange oil, which was subjected to flash chromatography on silica gel with dichloromethane-methanol (9:1) as eluant. Evaporation of the solvent in vacuo afforded 6 as a white hygroscopic solid (186 mg, 92%); mp dec>165° C.; Rf 0.23 [dichloromethane-methanol (9:1)]; For $C_{20}H_{28}N_2O_6$: calc 392.1947, found (M+Na) 415.1855; $\delta_H$ ($D_2O$) 1.16 (6H, s, 2×Ar—$CH_3$), 2.14 (3H, s, Ar—$CH_3$), 2.90 (3H, s, $OCH_3$), 3.02 (1H, dd, J 9.0 and 9.8, H-3), 3.17 (1H, dd, J 7.6 and 14.4, H-5), 3.30 (1H, dd, J 3.9 and 9.8, H-2), 3.35–3.56 (6H, m, H-4, H-6, and Ar—$CH_2$), 4.48 (1H, dd, J 9.0 and 9.8, H-3), 7.14 (1H, dd, J 1.6 and 7.8, H-6'), 7.56 (1H, d, J 1.6, H-4'), 7.65 (1H, d, J 7.8, H-7'); m/z (FAB) 415.1 (M+Na), 437.1 (M-H+2Na), 325.9, 199.0,176.0.

1-Ethyl-2,3,3-trimethyl-5-{[(3,4,5-trihydroxy-6-methoxy-tetrahydro-pyan-2-yl methyl)-carbamoyl]-methyl}-3H-indolium iodide 7

To a 25 ml flask, under argon, was added a stirring bar, 6 (150 mg, 0.38 mmol), acetonitrile (3 ml), and ethyl iodide (2.5 ml). The mixture was heated at reflux for 16 hours and was then cooled to room temperature. The volatile components were removed under high vacuum to give a pale brown residue, which was triturated with acetone (2×5 ml). The solid was dissolved in methanol (4 ml) and the solution was filtered. The methanol was removed in vacuo to afford 7 as a hygroscopic pale brown solid (180 mgs, 86%); Rf 0.26 [dichloromethanemethanol (8:2)]; $\delta_H$ ($D_2O$) 1.41 (3H, t, J 7.5, $CH_2C\underline{H}_3$), 1.44 (6H, s, 2×Ar—$CH_3$), 3.05 (3H, s, $OCH_3$), 3.10 (1H, dd, J 8.9 and 9.6, H-3), 3.21–3.30 (1H, m, H-5), 3.36 (1H, dd, J 3.8 and 9.8, H-2), 3.43–3.56 (3H, m, H-4 and H-6), 3.64 (2H, s, Ar—$CH_2$), 4.36 (2H, q, J 7.4, N—$CH_2$—), 4.57 (1H, d, J 3.7, H-1), 7.44 (1H, dd, J 8.3, 1.5, H-6'), 7.56 (1H, d, J 1.5, H-4'), 7.65 (1H, d, J 8.3, H-7'); m/z (FAB) 422.2 [(M+H)-I], 421.2 (M-I), 186.1.

1-(5-Carboxy-pentyl)-2,3,3-trimethyl-3H-indol-5-yl)-N-(3,4,5-trihydroxy-6-methoxy-tetrahydro-pyan-2-ylmethyl)-carbamoyl]-methyl}-3H-indolium iodide 8

To a 25 ml flask, under argon, was added a stirring bar, 6 (75 mg, 0.19 mmol), iodohexanoic acid (926 mg, 3.8 mmol), and nitromethane (2.5 ml). The mixture was heated at reflux for 16 hours and then cooled to room temperature. The solvent was removed in vacuo and the dark brown residue was partitioned between dichloromethane (30 ml) and water (50 ml). The aqueous was washed twice more with dichloromethane (2×30 ml) and was filtered. Removal of the water in vacuo gave a pale brown solid residue that was triturated with acetone (2×5 ml). The solid was dissolved in methanol (4 ml) and the solution was filtered. The methanol was removed in vacuo to afford 8 as a hygroscopic pale brown solid (98 mg, 81%); Rf 0.18 [dichloromethane-methanol (6:4)]; 8H ($D_2O$) 1.24–1.37 (2H, m, central $CH_2$), 1.42 (6H, s, 2×Ar—$CH_3$), 1.45–1.57 (2H, m, $C\underline{H}_2CH_2CO_2H$), 1.77–1.90 (2H, m, N—$CH_2C\underline{H}_2$), 2.20–2.29 (2H, m, C$\underline{H}_2CO_2H$), 3.00 (3H, s, $OCH_3$), 3.03–3.10 (H, m, H-3), 3.21–3.27 (1H, m, H-5), 3.34 (1H, dd, J 3.8 and 9.7, H-2), 3.41–3.56 (3H, m, H-4 and H-6), 3.62 (2H, s, Ar—$CH_2$), 4.33 (2H, t, J 7.5, N—$CH_2$), 4.54 (1H, d, J 3.8, H-1), 7.41 (1H, dd, J 1.5 and 8.4, H-7'), 7.53 (1H, d, J 1.5 and 8.4, H-4'), 7.61 (H, d, J 8.4, H-7'); m/z (FAB) 507.3 (M–I), 529.3, 272.2, 176.0.

5-{[(3,4,5-Trihydroxy-6-methoxy-tetrahydro-pyran-2-ylmethyl)-carbamoyl]methyl}-2-[3-(6-{[(3,4,5-trihydroxy-6-methoxy-tetrahydro-pyran-2ylmethyl)-carbamoyl]methyl}-3-ethyl-1,1-dimethyl-indan-2-ylidene)-propenyl]-1-ethyl-3,3-dimethyl-3H-indolium iodide 9

To a dry 10 ml flask, under argon, was added a stirring bar, 7 (19 mg, 3.5 μmol), pyridine (1 ml), and triethylorthoformate (100 μL). The mixture was stirred at room temperature for 5 minutes and was then heated at reflux for 90 minutes. The mixture was cooled to room temperature and the volatile components were removed under high vacuum. The dark purple residue was dissolved in the minimum mount of methanol and this solution was poured into stirred ether (100 ml.) The solid was filtered off and was subjected to reversed phase flash chromatography (50–80% methanol in water). The dye containing fractions were evaporated in vacuo and the residue was dissolved in methanol (2 ml). The solution was filtered and the methanol was removed in vacuo to afford 9 as a dark red solid (11.2 mgs, 66%); mp 163°–180° C. with dec.;Rf 0.08 [C18 $SiO_2$, water-methanol (1:1)]; For $C_{45}H_{63}N_4O_{12}I$ Calc. (M–I) 851.4442, found (M–I) 851.4417; $\delta_H$($D_2O$) 1.22 (6H, t, J 7.1, $CH_2C\underline{H}_3$), 1.57 (12H, s, 4×Ar—$CH_3$), (2H, b quintet, N—$CH_2C\underline{H}_2$), 2.95 (6H, s, $OCH_3$), 3.04 (2H, dd, J 8.9 and 9.7, H-3), 3.22 (2H, dd, J 7.7 and 14.1, H-5), 3.32 (2H, dd, J 3.7 and 9.8, H-2), 3.39–3.53 (10 H, m, H-4, H-6, and Ar—$CH_2$), 3.94 (4H, q, J 7.4, N—$CH_2$), 4.51 (2H, d, J 3.7, H-1), 6.14 (2H, d, J 13.6 , Ar—CH), 7.12 (2H, d, J 8.3, H-7'), 7.22 (2H, dd, J 1.5 and 8.3, H-6'), 7.32 (2H, d, J 1.5, H-4'), 8.23 (1H, t, J 13.5, Ar—CHC$\underline{H}$); m/z (FAB) 851.3 (M+H), 550.5.

2-[3-(3-(5-Carboxy-pentyl)-6-{[(3,4,5-trihydroxy-6-methoxy-tetrahydro-pyran-2-ylmethyl)-carbamoyl]methyl}-1,1-dimethyl-indan-2-ylidene)-propenyl]-1-ethyl-5-{[(3,4,5-trihydroxy-6-methoxy-tetrahydro-pyran-2-ylmethyl)-carbamoyl]methyl}-3,3-dimethyl-3H-indolium iodide 10

To a dry 25 ml flask, under argon, was added a stirring bar, 8 (35.5 mg, 56 μmol), 7 (32 mg, 55 μmol), pyridine (1 ml), and triethylorthoformate (250 μL). The mixture was stirred at room temperature for 5 minutes and was then heated at reflux for 75 minutes. The mixture was cooled to room temperature and the volatile components were removed under high vacuum. The dark purple residue was subjected to reversed phase flash chromatography (0–80% methanol in water). The unsymmetrical dye containing fractions were evaporated in vacuo to afford a dark red residue, which was dissolved in water (0.5 ml) and subjected to size exclusion chromatography on sephadex G15 (25×1 cm) with water as eluant. The dye containing fractions were evaporated in vacuo and the residue was dissolved in methanol (2 ml). The solution was filtered and the methanol was removed in vacuo to afford 10 as a dark red solid (14 mgs, 24%); mp 166°–179° C. with dec.; Rf 0.25 [C18 SiO$_2$, water-methanol (1:1)]; For C$_{49}$H$_{69}$N$_4$O$_{14}$I Calc. (M−I) 937.4810, found (M−I) 937.4799; UV-Vis 552 ∈: 135,000, 520(sh) ∈: 90,000; δ$_H$ (D$_2$O) 1.14 (3H, t, J 6.8, CH$_2$CH$_3$), 1.17–1.26 (2H, b quintet, central CH$_2$), 1.39–1.50 (14H, m, 4×Ar—CH$_3$ and CH$_2$CH$_2$CO$_2$H), 1.53–1.66 (2H, b quintet, N—CH$_2$CH$_2$), 2.09 (2H, t, J 7.2, CH$_2$CO$_2$H), 2.95 (6H, s, OCH$_3$), 3.04 (2H, t, J 9.2, H-3), 3.18 (2H, dd, J 7.5 and 14.1, H-5), 3.33 (2H, dd, J 3.8 and 9.3, H-2), 3.38–3.52 (10H, m, H-4, H-6, and Ar—CH$_2$), 3.78–3.92 (4H, bm, N—CH$_2$), 4.50 (2H, d, J 3.7, H-1), 6.04 and 6.07 (2H, overlapping d, J 13.3, Ar—CH), 7.03–7.09 (2H, m, H-7'), 7.11–7.17 (2H, m, H-6'), 7.24 (2H, s, H-4'), 8.19 (1H, t, J 13.3, Ar—CHCH); m/z (FAB) 937.5 (M−I).

1-(5-Carboxy-pentyl)-2-[3-(3-(5-carboxy-pentyl)-6-{[(3,4,5-trihydroxy-6-methoxy-tetrahydro-pyran-2-ylmethyl)-carbamoyl]methyl}-1,1-dimethyl-indan-2-ylidene)-propenyl]-5-{[(3,4,5-trihydroxy-6-methoxy-tetrahydro-pyran-2-ylmethyl)-carbamoyl]methyl}-3,3-dimethyl-3H-indolium iodide 11

To a dry 25 ml flask, under argon, was added a stirring bar, 8 (100 mg, 160 μmol), pyridine (1 ml), and triethylorthoformate (150 μL). The mixture was stirred at room temperature for 5 minutes and was then heated at reflux for 90 minutes. The mixture was cooled to room temperature and the volatile components were removed under high vacuum. The dark purple residue was subjected to reversed phase flash chromatography (0–50% methanol in water). The dye containing fractions were evaporated in vacuo to afford a dark red residue, which was dissolved in water (0.5 ml) and subjected to size exclusion chromatography on sephadex G15 (25×1 cm) with water as eluant. The dye containing fractions were evaporated in vacuo and the residue was dissolved in methanol (2 ml). The solution was filtered and the methanol was removed in vacuo to afford 11 as a dark red solid (21 mgs, 23%); mp 181°–198° C. with dec.; Rf 0.55 [C18 SiO$_2$, water-methanol (1:1)]; For C$_{53}$H$_{75}$N$_4$O$_{16}$I Calc. (M−I) 1023.5178, found (M−I) 1023.5173; δ$_H$ (D$_2$O) 1.17–1.26 (4H, m, central CH$_2$), 1.40–1.52 (16H, m, Ar—CH$_3$ and CH$_2$CH$_2$CO$_2$H), 1.57–1.68 (4H, m, N—CH$_2$CH$_2$), 2.09 (4H, t, J 7.3, CH$_2$CO$_2$H), 2.95 (6H, s, OCH$_3$), 3.03 (2H, t, J 9.3, H-3), 3.17 (2H, dd, J 7.7 and 14.4, H-5), 3.31 (2H, dd, J 3.8 and 9.7, H-2), 3.37–3.52 (10H, m, H-4, H-6, and Ar—CH$_2$), 3.87 (4H, bt, N—CH$_2$), 4.50 (2H, d, J 3.7, H-1), 6.04 (d, J 13.4, Ar—CH), 7.06 (2H, d, J 8.3, H-7'), 7.17 (1H, dd, J 0.8 and 8.3, H-6'), 7.26 (2H, d, J 0.8, H-4'), 8.23 (2H, t, J 13.5, Ar—CHCH); m/z (FAB) 1023.5 (M−I).

Active Ester 12

To a dry 1 ml microscale reaction vial was added dye 10 (11.8 mg, 12.1 μmol), tetramethyl(succinimido)uronium tetrafluoroborate (11.2 mg, 37.2 μmol), dry DMF (120 μL), and DIEA (10 μL). The vial was sealed and the mixture was stirred at room temperature for 1 hour. The mixture was transferred to a 25 ml round bottom flask using acetonitrile (400 μL) and the volatile components were removed under high vacuum. The residue was treated with acetonitrile (200 μl) and ether (10 ml) was added to precipitate the dye components. The supernatant liquid was removed via a filter tipped cannelating needle. Acetonitrile was added again and the dye components were precipitated by addition of ether. The supernatant liquid was removed as before. The solid residue was washed twice with dichloromethane (2×3 ml), was dried under high vacuum for 30 minutes, and was then treated with water (300 μL). The mixture was filtered through a cotton wool plug and was lyophilized to afford the active ester (12.2 mg, 95%), Rf 0.12 [C18 SiO$_2$, water-methanol (1:1)].

1-(2-Carboxy-ethyl)-2,3,3-trimethyl-3H-indolenium iodide 13

Trimethylindole (3) (2.0g, 12.5 mmol) and iodopropionic acid were mixed in a 100 ml flask with acetonitrile (40 ml). The mixture was heated at reflux for 18 hours and then concentrated to approximately 8 ml in vacuo. The solution was added dropwise to stirred ether (100 ml) and stirring was continued for 30 minutes. The ether was decanted and the residue was triturated with ether until a solid formed. The solid was filtered off and was washed with ether to afford 13 as a pale brown solid (1.55 g, 34%).

1-(10-tert-Butoxycarbonyl-decyl)-2,3,3-trimethyl-3-H-indolenium iodide 14

$^t$Butyl iodoundecanoate (1.13 g, 3.07 mmol) and trimethylindole (3) (1.0 g, 6.29 mmol) were dissolved in acetonitrile (30 ml) and the mixture was heated at reflux for 72 hours. The cooled reaction mixture was concentrated to about 3 ml and then added dropwise to stirred hexanes (100 ml). Stirring was continued for 1 hour and then the clear supernatant liquid was decanted. The residue was treated with ether (60 ml) and the mixture was stirred for 1 hour. The ether was decanted and the residue was washed twice more with ether (2×60 ml). The residue was dissolved in chloroform and the solution was filtered. Evaporation of the solvent in vacuo afforded 14 as a pale brown oil (1.44 g, 89%); Rf 0.30 [SiO$_2$, dichloromethane-methanol (19:1)]; for C$_{26}$H$_{42}$NO$_2$I calc. (M−I) 455.2260, found (M−I) 400.3230; δ$_H$ (CDCl$_3$) 1.22–1.58 (23H, m), 1.66 (6H, s), 1.86–1.98 (2H, m), 2.17 (2H, t, J 8), 3.10 (3H, s), 4.66 (2H, t, J 8), 7.55–7.69 (4H, m); δ$_C$17.2, 23.3, 25.0, 26.8, 28.0, 28.2, 29.0, 29.07, 29.13, 29.2, 35.6, 50.4, 53.3, 54.7, 79.9, 115.4, 123.3, 129.5, 130.2, 141.1, 141.8, 173.1, 195.7; m/z (FAB) 400.3 (100%), 344.2.

1,2,3,3-Tetramethyl-3H-indolenium iodide 15

Trimethylindole (3) was heated with 5 equivalents of methyl iodide at reflux for 18 hours and then the volatile components were removed in vacuo. The residue was triturated with ether until a solid formed. The solid was filtered off and was washed with ether to afford 15 as a pale brown solid.

1-(10-tert-Butoxycarbonyl-decyl)-2-{3-[1-(2-carboxy-ethyl)-3,3-dimethyl-1,3-dihydro-indol-2-ylidene]-propenyl}-3,3-dimethyl-3H-indolium iodide 16

13 (228 mg, 0.64 mmol) and 14 (167 mg 0.32 mmol) were dissolved in pyridine (4 ml) and triethylorthoformate (0.25 ml, 1.51 mmol) was added. The mixture was heated at reflux for 1 hour and then a second portion of triethylorthoformate (0.40 ml, 2.4 mmol) was added. Heating was continued for 90 minutes and then the pyridine was removed in vacuo. The residue was washed with hexanes (2×20 ml) and was subjected to flash chromatography on silica gel using dichloromethane-methanol (9:1) as eluant. Evaporation of the eluant in vacuo afforded 16 as a red solid (110 mg, 44%); Rf 0.28 [SiO$_2$, dichloromethane-methanol (9:1)]; for $C_{41}H_{57}N_2O_4I$ calc. (M) 768.3363, found (M−I) 641.4300; $\delta_H$ (CDCl$_3$) 1.15–1.23 (10H, m), 1.34–1.44 (13H, m), 1.63–1.83 (14H, m), 2.10 (2H, t, J 7.5), 2.74 (2H, t, J 7.4), 4.04 (2H, t, J 7.3), 4.39 (2H, t, J 7.4), 6.43 (1H, d, J 13.3), 6.61 (1H, d, J 13.5), 7.08 (1H, d, J 8.1), 7.14–7.23 (2H, m), 7.27–7.38 (5H, m), 8.33 (1H, t, J 7.4); m/z (FAB) 641.4 (100%).

1-(10-tert-Butoxycarbonyl-decyl)-2-[3-(3,3-dimethyl-1-{2-[(6-deoxy-β-cyclodextrin)-carbamoyl]-ethyl}-1-,3-dihydro-indol-2-ylidene)-propenyl]-3,3-dimethyl-3H-indolium iodide 17

To a dry 5 ml flask was added dye 16 (36.6 mg, 0.047 mmol) 6-amino-β-cyclodextrin (49.3 mg, 0.048 mmol), hydroxybenzatriazole (7.7 mg, 0.057 mmol) and dry DMF (1.5 ml). The mixture was cooled in an ice bath for 15 minutes and then DCC (11.8 mg, 0.057 mmol) was added. The mixture was stirred at 0° C. for 4 hours and then at room temperature for 78 hours. The solvent was removed under high vacuum without heating and the residue was washed with acetone (4×25 ml). The residue was subjected to repeated column chromatography on Sephadex LH-20 (3.5× 30 cm) using methanol-water (1:1) as eluant to afford 17 as a red solid (24 mg, 27%); Rf 0.18 [C18 SiO$_2$, water-methanol (2:8)]. For $C_{83}H_{126}N_3O_{37}I$ calc. (M) 1883.7114, found (M−I) 1756.8006.

1-(10-tert-Butoxycarbonyl-decyl)-2-[3-(3,3-dimethyl-1-{2-[(6-deoxy-β-cyclodextrin)-carbamoyl]-ethyl}-1-,3-dihydro-indol-2-ylidene)-propenyl]-3,3-dimethyl-3H-indolium iodide 18

17 was dissolved in 0.1M NaOH solution containing approximately 5% methanol and the mixture was stirred at room temperature for 18 hours. The solution was neutralized by addition of 1M HCl and was then diluted to 100 ml with water. This solution was loaded onto a column of reversed phase (C18) silica gel (1×7 cm) and the column was eluted with water (150 ml), 3:7 methanol-water (60 ml), 1:1 methanol-water (100 ml), and 8:2 methanol-water (30 ml). The deep red band was collected and the eluant was evaporated in vacuo without heating. The residue was taken up in methanol (2 ml) and the solution was filtered. The solvent was removed in vacuo and the residue was taken up in water (2 ml) and the solution was filtered. The solvent was removed in vacuo to afford 18 as a red solid; Rf 0.58 [C18 SiO$_2$, water-methanol (2:8)]; for $C_{79}H_{118}N_3O_{37}I$ calc (M−I) 1700.7443, found (M−I)1700.7484; $\delta_H$ (D$_2$O) 0.60–1.22 (10H, m), 1.43 (2H, quintet, J 7.2), 1.58–1.77 (14H, m), 2.04 (2H, t, J 7.7), 2.47–2.75 (4H, m), 3.06–3.81 (42H, m), 4.03–4.16 (2H, m), 4.23–4.30 (2H, m), 4.82 (1H, D, J 3.4), 4.87–4.95 (6H, m), 5.97 (1H, d, J 13.4), 6. 17 (1H, d, J 13.3), 7.16–7.51 (8H, m), 8.37 (1H, t, J 13.2); m/z (FAB) 1701 (M−I+H).

1-(10-tert-Butoxycarbonyl-decyl)-2-{5-[1-(2-carboxy-ethyl)-3,3-dimethyl-1,3-dihydro-indol-2-ylidene]-penta-1,3-dienyl}-3,3-dimethyl-3H-indolium iodide 19

13 (266 mg, 0.74 mmol) and 14 (195 mg 0.37 mmol) were dissolved in methanol (20 ml). Trimethoxypropene (100 mg, 0.76 mmol) and potassium acetate (300 mg, 3.0 mmol) were added and the mixture was stirred at room temperature for 3 days. The solvent was removed in vacuo and the residue was subjected to flash chromatography on silica gel using dichloromethane-methanol (9:1) as eluant. Evaporation of the eluant in vacuo afforded 19 as a blue solid (134 mg, 46%); Rf 0.28 [SiO$_2$, dichloromethane-methanol (9:1)]; for $C_{43}H_{59}N_2O_4I$ calc. (M−I) 667.4475, found (M−I) 667.4462; $\delta_H$ (CDCl$_3$) 1.22–1.432 (4H, m), 1.47–1.58 (2H, m), 1.69–1.84 (14H, m), 2.17 (2H , t, J 7), 2.82 (2H, t, J 6), 3.97 (2H, t, J 7), 4.36 (2H, t, J 7), 6.12 (1H, d, J 14), 6.33 (1H, d, J 14), 6.65 (1H, t, J 12), 7.06 (2H, d, J 7),7.15–7.26 (2H, m), 7.29–7.39 (4H, m), 8.00–8.14, (2H, m); m/z (FAB) 667.5 (100%).

1-(10-tert-Butoxycarbonyl-decyl)-2-[5-(3,3-dimethyl-1-{2-[(6-deoxy-β-cyclodextrin)-carbamoyl]-ethyl}-1-,3-dihydro-indol-2-ylidene)-penta-1,3-dienyl]-3,3-dimethyl-3H-indolium iodide 20

To a dry 5 ml flask was added dye 19 (45 mg, 0.057 mmol) 6-amino-β-cyclodextrin (64 mg, 0.057 mmol), hydroxybenzatriazole (15.3 mg, 0.114 mmol) and dry DMF (1.5 ml). The mixture was cooled in an ice bath for 15 minutes and then DCC (24 mg, 0.114 mmol) was added. The mixture was stirred at 0° C. for 4 hours and then at room temperature for 78 hours. The solvent was removed under high vacuum without heating and the residue was washed with acetone (4×25 ml). The solid was treated with methanol (2 ml) and the solution was filtered. The solvent was removed in vacuo and the residue was subjected to chromatography on Sephadex LH-20 (3.5×30 cm) using methanol-water (1:1) as eluant. The major blue band was collected and the residue, after evaporation of the solvent, was subjected to chromatography on reverse phase (C18) silica gel with 4:6 methanol-water and then 8:2 methanol-water as eluant. The solvent was removed in vacuo and the residue was taken up in methanol (2 ml) and the solution was filtered. The solvent was removed in vacuo and the residue was taken up in water (2 ml), and this solution was filtered. The solvent was removed in vacuo to afford 20 as a blue solid (52 mg, 48%); Rf 0.18 [C18 SiO$_2$, water-methanol (2:8)]; for $C_{85}H_{128}N_3O_{37}I$ calc (M−I) 1782.8227, found (M−I)+1782.8262; $\delta_H$ (D$_2$O/CD$_3$CN (1:2)) 1.17–1.28 (12H, m), 1.31–1.41 (11H, m), 1.58–1.77 (14H, m), 2.03 (2H, t, J 7), 2.61 (2H, bt), 3.18–3.26 (2H, m), 3.35–3.77 (42H, m), 4.02 (2H, bt), 4.76 (1H, d, J 4), 4.82 (1H, d, J 4), 4.86–4.92 (5H, m), 6.11 (1H, d, J 14), 6.24 (1H, d, J 14), 6.27 (1H, t, J 12), 7.14–7.27 (4H, m), 7.30–7.88 (4H, m), 7.94–8.08 (2H, m); m/z (FAB) 1782.5.

1-(10-tert-Butoxycarbonyl-decyl)-2-[5-(3,3-dimethyl-1-{2-[(6-deoxy-β-cyclodextrin)-carbamoyl]-ethyl}-1-,3-dihydro-indol-2-ylidene)-penta-1,3dienyl]-3,3-dimethyl-3H-indolium iodide 21

20 (35 mg, 0.018 mmol) was dissolved in 85% formic acid (4 ml) and the solution was stirred at room temperature for 20 hours. The volatile components were removed under high vacuum without heating. The solid residue was dissolved in a mixture of methanol (1 ml), DMF (1 ml), and carbonate-bicarbonate buffer pH 9.5 (15 ml), and this solution was stirred at room temperature for 40 hours. The solution was neutralized by addition of 1M HCl and was diluted to 100 ml with water. This solution was loaded onto a column of reversed phase (C18) silica gel (1×7 cm) and the column was eluted with water (150 ml), 3:7 methanol-water (60 ml), 1:1 methanol-water (100 ml), and 8:2 methanol-water (30 ml). The deep blue band was collected and the eluant was evaporated in vacuo without heating. The residue was taken up in methanol (2 ml) and the solution was filtered. The solvent was removed in vacuo and the residue was taken up in water (2 ml), and this solution was filtered. The solvent was removed in vacuo to afford 21 as a blue solid; Rf 0.58 [C18 SiO$_2$, water-methanol (2:8)]; for C$_{85}$H$_{128}$N$_3$O$_{37}$I calc (M–I) 1726.7600, found (M–I)+ 1726.7563; δ$_H$ (D$_2$O/CD$_3$CN (1:2)) 1.40–1.70 (12H, m), 1.84–2.17 (16H, m), 2.47 (2H, t, J 8), 2.96–3.05 (2H, m), 3.67 (2H, t, J 9), 3.76–4.23 (42H, m), 4.44–4.51 (2H, m), 5.19 (5.36, m), 6.45 (1H, d, J 14), 6.71 (1H, d, J 14), 6.89 (1H, t, J 15), 7.57–7.71 (4H, m), 7.74–7.91 (4H, m), 8.35–8.50 (2H, m); m/z (FAB) 1727.9.

3[2-(2,3,3-trimethyl-3H-indol-5-yl)-acetylamino]-propionic acid tert-butyl ester 22

Carboxymethylindole 4 (543 mg, 2.5 mmol), hydroxysuccinimide (575 mg, 5.0 mmol), and dry dichloromethane (5 ml) were mixed in a 25 ml flask, under argon, and the flask was cooled in an ice bath. After 10 minutes, DCC (703 mg, 3.4 mmol) was added and stirring was continued at 0° C. for 4 hours. The mixture was stirred for a further 16 hours at room temperature. The solid was filtered off and was washed with dry dichloromethane (5 ml). The solution was concentrated to about 2 ml and then 'butyl-b-alinate hydrochloride (452 mg, 2.5 mmol) and triethylamine (0.40 ml) were added. The mixture was stirred for 40 hours. The solid was filtered off and was washed with dichloromethane (4 ml). The solvent was removed in vacuo and the residue was subjected to flash chromatography on silica gel using dichloromethane-methanol (19:1) as eluant. Evaporation of the solvent afforded 22 as a pale yellow oil (750 mg, 87%); Rf 0.20 [SiO$_2$, dichloromethane-methanol (19:1)]; for C$_{20}$H$_{28}$N$_2$O$_3$ calc. (M+.) 344.2100, found (M+.) 344.2101; δ$_H$ (CDCl$_3$) 1.31 (6H, s), 1.36 (9H, s,), 2.31 (3H, s,), 2.39 (2H, t, J 6), 3.44 (2H, quartet, J 6), 3.58 (2H, s), 6.35 (1H, bt), 7.14–7.20 (2H, m), 7,51 (1H, d, J 8); δ$_C$ 15.2, 23.0, 28.0, 35.1, 35.2, 43.8, 53.6, 80.9, 120.1, 122.3, 129.6, 131.9, 146.5, 152.9, 170.9, 171.5, 188.0; m/z (EI) 173 (100%) 199, 288.

5-[(2-tert-Butoxycarbonyl-ethylcarbomyl)-methyl]-1,2,3,3-tetramethyl-3H-indolium iodide 23

22 (847 mg, 2.46 mmol) and methyl iodide (1.05 g, 7.38 mmol) were dissolved in acetonitrile (20 ml) and the mixture was heated at 40° C. for 16 hours. The volatile components were removed in vacuo and the residue was dissolved in dichloromethane (2 ml). This solution was added dropwise to stirred ether (100 ml) and stirring was continued until the supernatant liquid was clear. The solid was filtered off to afford 23 as a pale brown solid (1.10 g, 92%); Rf 0.5 [SiO$_2$, dichloromethane-methanol (9:1)]; For C$_{21}$H$_{31}$N$_2$O$_3$I Calc. (M–I) 359.2335, found (M–I) 359.2345; δ$_H$ (CDCl$_3$) 1.38 (9H, s), 1.53 (6H, s), 2.45 (2H, t, J 6.9), 3.38 (2H, quartet, J 6.5),3.66 (2H, s), 4.05 (3H, s), 7.30 (1H, t, J 5.7), 7.46–7.56 (2H, m ), 7.65 (1H, s); δ$_C$ (CD$_3$CN)15.4, 22.7, 28.4, 36.2, 36.3, 36.4, 43.4, 55.4, 81.2, 115.8, 125.3, 131.1, 140.0, 141.9, 142.9, 170.8, 172.0, 196.7; m/z (FAB) 359.2 (M–I).

5-[(2-tert-Butoxycarbonyl-ethylcarbomyl)-methyl]-1-(2-carboxy-ethyl)-2,3,3-trimethyl-3H-indolium iodide 24

22 (300 mg, 0.96 mmol) and iodopropionic acid (600 mg, 3.0 mmol) were dissolved in acetonitrile (20 ml) and the mixture was heated at reflux for 48 hours. The mixture was concentrated in vacuo to about 3 ml and then was added dropwise to stirred ether (100 ml). Stirring was continued until the supernatant liquid was clear, and then this liquid was decanted. The residue was subjected to flash chromatography on silica gel using dichloromethane-methanol (8:2) as eluant. Evaporation of the solvent afforded 24 as a pale brown solid (305 mg, 60%); Rf 0.2 [SiO$_2$, dichloromethane-methanol (8:2)]; for C$_{23}$H$_{33}$N$_2$O$_5$I calc. (M–I) 417.2389, found (M–I) 417.2389; δ$_H$ (CD$_3$CN+3 drops D$_2$O) 1.37 (9H, s), 1.50 (6H, s), 2.36 (2H, t, J 7), 2.98 (2H, t, J 7), 3.27–3.34 (2H, m), 3.57 (2H, s), 4.57 (2H, t, J 7), 7.16–7.24 (1H, bm), 7.47 (1H, dd, J 8 and 1), 7.60 (1H, d, J 1), 7.67 (1H, d, J 8); m/z (FAB) 417.2 (M–I).

5-[(2-tert-Butoxycarbonyl-ethylcarbomyl)-methyl]-1-(2-carboxy-ethyl)-3,3-dimethyl-2-dimethyl-2-[5-(1,3,3-trimethyl-1,3-dihydro-indol-2-ylidene]-penta-1,3-dienyl]-3H-indolium iodide 25

24 (180 mg, 0.331 mmol) and 15 (200 mg, 0.662 mmol) were dissolved methanol (15 ml). Trimethoxypropene (90 mg, 0.68 mmol) and potassium acetate (300 mg, 3 mmol) were added and the mixture was heated at reflux for 16 hours. The solvent was removed in vacuo and the residue was treated with dichloromethane (40 ml) The solid was filtered off and was washed with dichloromethane. The solvent was removed in vacuo and the residue was subjected to flash chromatography on silica gel using dichloromethane-methanol (9:1) as eluant. Evaporation of the solvent afforded 25 as a blue solid (76 mg, 30%); Rf 0.17 [SiO$_2$, dichloromethane-methanol (9:1)]; for C$_{38}$H$_{48}$N$_3$O$_5$I calc 626.3594, found 626.3585; δ$_H$ (CDCl$_3$) 1.35 (9H, s), 1.61 and 1.63 (12H, 2×s), 2.44 (2H, t, J 7), 2.64–2.76 (2H, bm), 3.36–3.45 (2H, m), 3.53 (2H, s), 3.55 (3H, s), 4.24–4.42 (2H, bm), 6.03 (1H, d, J 13), 6.33 (1H, d, J 13), 6.55 (1H, t, J 12), 7.05–7.40 (7H, m), 7.44–7.54 (1H, bm), 7.87 (2H, quartet, J 13); δ$_C$ 27.8, 28.0, 31.6, 34.9, 35.2, 35.4, 42.5, 43.0, 48.9, 49.6, 80.5, 102.5, 104.5, 110.1, 111.4, 122.0, 123.3, 124.7, 125.6, 128.5, 129.9, 133.9, 140.6, 140.9, 141.5, 142.8, 152.3, 153.6, 170.6, 171.3, 172.2, 173.7; m/z (FAB) 626.3 (M–I).

5-[(2-tert-Butoxycarbonyl-ethylcarbomyl)-methyl]-2-{5-[1-(2-carboxy-ethyl)-3,3-dimethyl-1,3-dihydro-indol-2-ylidene]-penta-1,3-dienyl}-1,3,3-trimethyl-3H-indolium iodide 26

23 (310 mg, 0.639 mmol) and 13 (460 mg, 1.28 mmol) were dissolved in methanol (20 ml). Trimethoxypropene (190 mg, 1.44 mmol) and potassium acetate (600 mg, 6.1 mmol) were added and the mixture was heated at reflux for 16 hours. The solvent was removed in vacuo and the residue was treated with dichloromethane (40 ml). The solid was filtered off and was washed with dichloromethane. The solvent was removed in vacuo and the residue was subjected to flash chromatography on silica gel using dichloromethane-methanol (8:2) as eluant. Evaporation of the solvent afforded 26 as a blue solid (240 mg, 50%); Rf 0.36 [SiO$_2$, dichloromethane-methanol (8:2)]; For C$_{38}$H$_{48}$N$_3$O$_5$I Calc. (M–I) 626.3593, found (M–I) 626.3585; δ$_H$ (CD$_3$CN+5 drops D$_2$O) 1.34 (s, 9H), 1.57 and 1.58 (2×s, 12H), 2.33 (2H, t, J 6), 2.48–2.57 (2H, bm), 3.25–3.32 (2H, m), 3.44 (2H, s), 3.47 (3H, s), 4.14–4.24 (2H, bm), 6.14 (1H, d, J 14), 6.25 (1H, d, J 14), 6.52 (1H, t, J 12), 7.10–7.41 (7H, m), 7.90–8.04 (2H, m); δ$_C$ 27.8, 27.9, 28.3, 32.1, 35.5, 36.0, 36.4, 42.5, 43.3, 50.2, 82.0, 104.1, 104.3, 111.8, 112.2, 123.2, 124.1, 126.0 (2C), 129.7, 130.4, 133.8, 142.4, 142.6, 143.1, 143.2, 154.6, 154.7, 172.8, 173.0, 174.1, 175.0; m/z (FAB) 626.3 (M–I).

27 and 5-[(2-Carboxy-ethylcarbamoyl)-methyl]-3,3-dimethyl-1-{2-(6-deoxy-β-cyclodextrin)-carbamoyl]-ethyl}-2-[5-(1,3,3-trimethyl-1,3-dihydro-indol-2-ylidene]-penta-1,3-dienyl]-3H-indolium iodide 29

To a dry 5 ml flask was added dye 24 (45 mg, 0.060 mmol) 6-amino-β-cyclodextrin (71 mg, 0.063 mmol), hydroxysuccinimide (11 mg, 0.096 mmol) and dry DMF (1.5 ml). The mixture was cooled in an ice bath for 15 minutes and then DCC (19 mg, 0.092 mmol) was added. The mixture was stirred at 0° C. for 4 hours and then at room temperature for 78 hours. The mixture was added dropwise to stirred acetone (150 ml) and stirring was continued for 30 minutes. The solid was filtered off and was washed with acetone (4×25 ml). The residue was treated with methanol (40 ml) and after stirring for 20 minutes the mixture was filtered. The solvent was removed in vacuo to afford crude 27 as a blue solid. The crude material was dissolved in 85% formic acid (7 ml). This solution was stirred at room temperature for 20 hours and then the volatile components were removed under high vacuum without heating. The solid residue was dissolved in a mixture of methanol (1 ml), DMF (1 ml), and carbonate-bicarbonate buffer pH 9.5 (15 ml), and this solution was stirred at room temperature for 40 hours. The solution was neutralized by addition of 1M HCl and was diluted to 100 ml with water. This solution was loaded onto a column of reversed phase (C18) silica gel (1×7 cm) and the column was eluted with water (150 ml), 3:7 methanol-water (60 ml), 1:1 methanol-water (100 ml), and 8:2 methanol-water (30 ml). The deep blue band was collected and the eluant was evaporated in vacuo without heating. The residue was taken up in methanol (2 ml) and the solution was filtered. The solvent was removed in vacuo and the residue was taken up in water (2 ml) and this solution was filtered. Evaporation of the solvent in vacuo afforded 29 as a blue solid (10 mg, 9%); Rf 0.60 [C18 $SiO_2$, water-methanol (2:8)]. For $C_{76}H_{109}O_{38}N_4Cl$ (1721) calc. (M−Cl) 1685.6720, found (M−Cl) 1685.6689: m/z (FAB) 1685.5 (M−I).

5-[(2-tert-Butoxycarbonyl-ethylcarbomyl)-methyl]-2-[5-(3,3-dimethyl-1-{2-[(6-deoxy-β-cyclodextrin)-carbamoyl]-ethyl}-1,3-dihydro-indol-2-ylidene]-penta-1,3-dienyl]-3H-indolium iodide 28

To a dry 5 ml flask was added dye 26 (56,3 mg, 0.075 mmol), tetramethyl(succinimido)uronium tetrafluoroborate (60.2 mg, 0.20 mmol) and acetonitrile (0.50 ml). After stirring for 20 minutes DIEA (0.017 ml, 0.10 mmol) was added. Stirring was continued for 20 minutes. 6-Amino-β-cyclodextrin (113.3 mg, 0.10 mmol) was dissolved in DMSO (1 ml) and this solution was added to that of the dye. The mixture was stirred for 78 hours. The mixture was added dropwise to stirred acetone (150 ml) and stirring was continued for 30 minutes. The solid was filtered off and was washed with acetone (4×25 ml). The residue was treated with methanol (40 ml and after stirring for 20 minutes the mixture was filtered. The solvent was removed in vacuo and the residue was subjected to repeated column chromatography on Sephadex LH 20 (3.5×30 cm) using methanol-water (1:1) as eluant to afford 28 as a blue solid (56 mg, 40%). For $C_{80}H_{110}O_{38}N_4Cl$ calc. (M−Cl) 1741.7346, found (M−Cl) 1741.7392; $\delta_H$ ($D_2O/(CD_3)_2CO$ (1:2)) 1.27 (9H, s), 1.58 and 1.59 (12 H, 2×S), 2.35 (2H, t, J 7), 2.69–2.75 (2H, bs), 3.17–3.64(m), 4.81 (1H, d, J 3), 4.87 (1H, d, J 3), 4.92–4.94 (5H, bm), 6.26 (1H, d, J13), 6.33 (1H, d, J14), 6.62 (1H, t, J 12), 7.12–7.42 (7H, m), 8.10–8.25 (2H, m); m/z (FAB) 1742.1 (M−I).

5-[(2-Carboxy-ethylcarbomyl)-methyl]-2-[5-(3,3-dimethyl-1-{2-[(6-deoxy-β-cyclodextrin)-carbamoyl]-ethyl}-1,3-dihydro-indol-2-ylidene]-penta-1,3-dienyl]-3H-indolium iodide 30

28 (48 mg, mmol) was dissolved in 85% formic acid (8 ml) and the solution was stirred at room temperature for 20 hours. The volatile components were removed under high vacuum without heating. The solid residue was dissolved in a mixture of methanol (1 ml), DMF (1 ml), and carbonate-bicarbonate buffer pH 9.5 (15 ml), and this solution was stirred at room temperature for 40 hours. The solution was neutralized by addition of 1M HCl and was diluted to 100 ml with water. This solution was loaded onto a column of reversed phase (C18) silica gel (1×7 cm) and the column was eluted with water (150 ml), 3:7 methanol-water (60 ml), 1:1 methanol-water (100 ml), and 8:2 methanol-water (30 ml). The deep blue band was collected and the eluant was evaporated in vacuo without heating. The residue was taken up in methanol (2 ml) and the solution was filtered. The solvent was removed in vacuo and the residue was taken up in water (2 ml) and this solution was filtered. Evaporation of the solvent in vacuo afforded 30 as a blue solid (37 mg, 78%); Rf 0.60 [C18 $SiO_2$, water-methanol (8:2)]. For $C_{76}H_{109}O_{38}N_4Cl$ (1721) calc. (M−Cl) 1685.6720, found (M−Cl) 1685.6712, m/z (FAB) 1685.5 (M−I).

Dextran Labeling with reagent 12

To a solution of aminodextran (8.5 mg, 0.2 μmol) in 0.02M carbonate/bicarbonate buffer pH 9.5 (1.0 ml) was added a solution of active ester 12 (2.3 mg, 2 μmol) in DMF (50 μl). After mixing, the solution was allowed to stand overnight, and was then filtered. The solution was loaded onto a column of sephadex G50 (3.5×15 cm) and the column was eluted with buffer (10 mM Tris, 50 mM NaCl, 1 mM $NaN_3$, pH 7.5). The labeled dextran was collected ahead of the hydrolyzed labeling reagent. The solution was dialyzed against water (3×800 ml) and the aqueous solution was lyophilized to afford a the labeled dextran as a pink/red solid.

Protein Labeling with reagent 12

A stock solution of sheep IgG (m.w. 155,000) was prepared at a concentration of 4 mg/ml (approx. 2.6 μM) in a carbonate/bicarbonate buffer (0.02M, pH 9.5.) Aliquots (250 μL) of the stock were dispensed into vials. A stock solution of dye active ester 12 was prepared at a concentration of 5 mM (approx. 1 mg/200 μL) in water. Aliquots of the dye stock solution were added to those of the protein to afford a series of starting dye to protein ratios in the range 1.5:1 to 20:1. The solutions were mixed well and left to stand at room temperature overnight. The samples were filtered and then were loaded onto a column of sephadex G50 (0.7×12 cm) which was eluted with PBS (pH 7.5). The labeled protein was collected ahead of the hydrolyzed dye and was studied without further purification.

Dextran Labeling with compounds 18, 21, 29 and 30

Procedure 1—Example of preactivation using compound 21. Compound 21 (5.5 mg, mmol) and tetramethyl (succinimido)uronium tetrafluoroborate (6 mg) were dissolved in DMF (0.15 ml) and the mixture was stirred for 5 minutes. DIEA (0.004 ml) was added and stirring was continued for 2 hours. Ethyl acetate (3 ml) was added to cause precipitation of the products. The suspension was centrifuged and the supernatant was removed. The solid was washed with ethyl acetate twice more (2×3 ml), and then with acetonitrile (3×3 ml) to afford the crude reactive compound, which was used without further purification. This reagent (2.5 mg) was added to aminodextran (25 mgs, mmol) dissolved in carbonate bicarbonate (0.50 ml) buffer pH 9.5. DMF (0.05 ml) was added and after mixing the solution was left to incubate for 18 hours. The mixture was loaded onto a column of Sephadex G50 in PBS. Elution with PBS afforded the labeled dextran.

Procedure 2—Example of in situ labeling using compound 30. Aminodextran (10 mgs) was dissolved in carbonate bicarbonate buffer pH 9.5 (0.50 ml). Compound 30 (1.7 mg) and tetramethyl(succinimido)uronium tetrafluoroborate (3.5 mg) were added. After mixing, the solution was left to stand at room temperature over night. The mixture was loaded onto a column of Sephadex G50 in PBS. Elution with PBS afforded the labeled dextran.

What is claimed is:

1. A method for imparting fluorescent properties to a target material, the method comprising the steps of incubating:

(i) a target material having at least one functional group selected from the group consisting of carboxylic acid, alkyl halide, aldehyde, ketone, amino, or sulphydryl or having at least one reactive group that can covalently bond with said at least one functional group, and;

(ii) an amount of a glycoconjugate fluorescent compound having the formula:

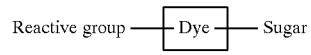

wherein dye is a fluorophone;

sugar is a sugar or modified carbohydrate rendering the glycoconjugate soluble in aqueous media; and Reactive group is a functional group selected from the group consisting of succinimidyl ester, carboxylic acid, isothiocyanate, haloacetamide, maleimide, alkyl halide, azido, hydrazido, aldehyde, ketone, amino sulphydryl, provided said reactive group can covalently bond with said at least one functional group;

for a period of time sufficient to permit said at least one functional or reactive group of said fluorescent compound to covalently bond to said at least one reactive or functional group of said target material.

* * * * *